United States Patent
Cardarelli

(10) Patent No.: US 6,718,981 B2
(45) Date of Patent: Apr. 13, 2004

(54) DENTAL MASK

(76) Inventor: Venanzio Cardarelli, 20 N. Triangle Dr., Plymouth, MA (US) 02301

( * ) Notice: Subject to any disclaimer, the term of this patent is extended or adjusted under 35 U.S.C. 154(b) by 158 days.

(21) Appl. No.: 10/072,280

(22) Filed: Feb. 7, 2002

(65) Prior Publication Data

US 2003/0145858 A1 Aug. 7, 2003

(51) Int. Cl.[7] .......................... A62B 7/10; A62B 18/02; A62B 23/02
(52) U.S. Cl. .................. 128/206.19; 128/205.27; 128/205.29; 128/206.13; 128/206.23
(58) Field of Search .............. 128/205.27, 205.29, 128/206.12, 206.13, 206.16, 206.19, 206.26, 206.28, 207.11, 206.23, 206.17, 206.18, 206.24, 863

(56) References Cited

U.S. PATENT DOCUMENTS

| | | | | |
|---|---|---|---|---|
| 893,213 A | * | 7/1908 | Whiteway | 128/206.16 |
| 925,409 A | * | 6/1909 | Woolf et al. | 128/206.16 |
| 1,150,991 A | * | 8/1915 | Britton | 128/206.19 |
| 1,562,302 A | * | 11/1925 | Dean et al. | 128/206.13 |
| 2,039,681 A | * | 5/1936 | Chatfield | 128/206.19 |
| 4,240,420 A | * | 12/1980 | Riaboy | 128/206.14 |
| 4,606,341 A | | 8/1986 | Hubbard et al. | |
| 4,951,662 A | | 8/1990 | Townsend, Jr. | |
| 5,307,796 A | | 5/1994 | Kronzer et al. | |
| 5,331,957 A | * | 7/1994 | Liu | 128/206.15 |
| 5,406,944 A | | 4/1995 | Gazzara | |
| 5,584,078 A | | 12/1996 | Saboory | |
| 5,699,792 A | | 12/1997 | Reese et al. | |
| 5,842,470 A | * | 12/1998 | Ruben | 128/206.19 |
| 6,584,976 B2 | * | 7/2003 | Japuntich et al. | 128/206.15 |

* cited by examiner

Primary Examiner—Weilun Lo
Assistant Examiner—Darwin P Erezo
(74) Attorney, Agent, or Firm—D. Michael Burns

(57) ABSTRACT

A dental mask which has two separate chambers, one for inhalation and the other for exhalation. The two separate chambers being separated by an elasticized strip across the philtrum area. The mask is designed to be disposable, yet also have the ability to accept, for increased protection, filter insertable pads which can be placed in the inner surface of the mask. An embodiment of the mask would allow the main frame to be reusable, by having means for snapping a disposable filter onto the frame.

16 Claims, 6 Drawing Sheets

DENTAL MASK

BACKGROUND OF THE INVENTION

1. Field of the Invention

The present invention relates generally to a dental mask that is designed to be worn by members of a dental staff, and more specifically to a dental mask having dual chambers, one for inhaling and the other for exhaling.

2. Description of the Prior Art

The environment in a dental office can be detrimental to the health of both the patient and the dental staff. In addition to harmful aerosols, which studies have shown may contain up to 100,000 bacteria per cubic foot of air within three feet of the patient, the dental office may regularly contain nitrous gases, disinfectant fumes, mercury vapors, sterilization fumes, tooth dusts, fillings dust, sulfates, polyether fumes, viruses, saliva droplets, etc. The aerosols generated by air polishers are particularly harmful. High speed cutting instruments (200,000 to 300,000 rpm) generate considerable heat which can cause injury to the tooth pulp. To prevent this, water spray is employed as a coolant and a lubricant. As a result, there are microbial aerosols which are generated from the patient's mouth during dental operations which are comparable in bacterial concentrations to those produced during coughing and sneezing.

Transmission of infection requires a series of factors: a source of reservoir for the pathogen, a pathogen of sufficient infectivity and number, a mode of escape from the host, and a portal of entry. Infection-control techniques seek to eliminate one or more links in the chain of infection. Barrier products such as masks are viewed as a means of protecting both patients and dental staff from pathogens in potentially infectious sprays, splash, and spatter. Masks must be worn when risk of spray or splash of fluids can be anticipated. The FDA recommends that surgical masks have a 95 percent or greater bacterial filtration efficiency. Masks of glass or synthetic fiber demonstrate great filtering efficiency. However, almost all the particles that can penetrate an efficient filtration mask are so small in diameter that they will be hazardous if they penetrate the alveoli of the human lungs. It is important to consider that bacterial aerosols do remain airborne for many hours after certain dental procedures, unless they are removed by an efficient ventilation system.

The prior art is well documented with masks that attempt to solve the above problems. In addition to filtration, masks seek to solve the problems such as fogging of eye glasses. Some short comings in prior art masks are masks that do not adapt very well to different sizes and shapes of faces, especially along the ridge of the nose or chin. Many masks do not provide any measure near the 95 percent FDA requirement. The fogging of glasses is due to the carbon dioxide along with warm moisture that accompanies the breath in exhalation. Lack of proper venting of the mask may cause members of the dental staff to breath in his/her own exhaled carbon dioxide, thereby diminishing the percentage of oxygen with each breath. This lack of oxygen can cause symptoms of hypoxia; that is the state in which there is inadequate oxygen to satisfactory meet the needs of tissues. The effects of long term state of hypoxia can be seen in drowsiness, inattentiveness, apathy, delayed reaction time, severe fatigue and reduced work capacity.

For an average person the intake of air with each inhaled breath is approximately 500 ml, of which about 150 ml is expired before it ever reaches the alveoli. This 150 ml of air is considered useless from the point of view of oxygenating the blood and the respiratory passageways are thereby called dead space. Thus for each breath only about 350 ml of air are actually utilized. Since the average person needs about 4200 ml of new air per minute, this will require about 12 breaths per minute. In a dental procedure, if the mask does not properly ventilate the exhaled breath, then the dentist will breathe in a percentage of his own carbon dioxide with each breath, thereby requiring far more respirations per minute to satisfy his/her oxygen requirements to thereby prevent a state of transient hypoxia.

There are basically two types of masks used in dental procedures. One is a semirigid cup-shaped mask that fits over the nose and mouth, usually with some form of a malleable soft metal to pinch over the ridge of the nose to prevent fogging. The other is a softer mask which is predominantly made of pleated layers of filter material. The main advantage of the semirigid mask is that it will keep the inner surface away from the wearer's face. The biggest disadvantage is that both fresh air and exhale breath can mingle together in the chamber. The main advantage of the softer pleated mask is in comfort to the wearer. The problem is that, when the wearer inhales, these masks have a tendency to be drawn very close to the face, thereby creating a somewhat claustrophobic feeling, as well as the problem created when a very strong inhalation adheres a large amount of particles at the mouth or nose sites.

U.S. Pat. No. 5,307,796 issued to Kronzer et al. on May 3, 1994, discloses a face mask of the semirigid type that is very commonly found in dental offices. It is generally the least expensive and has only one chamber.

U.S. Pat. No. 4,951,662 issued to Townsend, Jr. on Aug. 28, 1990, teaches the use of a mask that seeks to eliminate fogging by having a housing adjacent to the mask which has a volume considerably larger than the mask volume, thereby permitting the breath to be substantially removed during each breathing cycle. Townsend, Jr. shows a loop encircling the wearer's neck and suggests the use of a circulating fan to draw in fresh air.

U.S. Pat. No. 5,699,792 issued to Reese et al. on Dec. 23, 1997, discloses a face mask with enhanced facial sealing. The mask to Reese is typical of the softer pleated masks which are available and address the need for improved facial sealing to protect against bacteria, viruses, particles, blood droplets, contaminants etc.

U.S. Pat. No. 4,606,341 issued to Hubbard et al. addresses the importance of keeping the mask from collapsing against the wearer's face, but this patent falls short of suggesting dual chambers.

U.S. Pat. No. 5,406,944 issued to Gazzara on Apr. 18, 1995, teaches the use of an adjustable face protector which provides increased prevention from contaminated fluids. The present invention addresses the use of shields as well as filtration capturing and reflective panels.

U.S. Pat. No. 5,584,078 issued to Saboory on Dec. 17, 1996, suggests the use of a detachable/disposable face shield that one can clip to a surgical mask. This patent addresses the need for a shield, mainly for the eyes, in which can be used according to the needs of the wearer.

None of the above inventions and Patents, taken either singly or in combination, is given to describe the instant invention as claimed.

SUMMARY OF THE INVENTION

Accordingly, the above problems and difficulties are obviated by the present invention which provides for a primary disposable face mask, as well as a reusable frame to be used by medical personnel, especially those in the dental profession.

More particularly, the present invention is comprised of a face mask having dual chambers. An upper chamber for inhalation of fresh air and a lower chamber for exhalation of carbon dioxide ladened breath. The lower chamber having vent flap openings on the cheek sides for the removal of spent air. Embodiments of the present invention may have tubing attached to the vent openings for releasing of the exhaled breath away from the work site. In some embodiments the tubing can be attached to an exhaust suction lines or filtration systems. The dual chambers are created by mask design and by having a band of soft elastic material across the philtrum (area between naris and upper lip) which effectively seals the two chambers from each other. By inhaling through the upper chamber, the incoming air to the lungs will not be contaminated or mixed with exhaled carbon dioxide and other unwanted substances. In lieu of the vent flaps of the preferred embodiment, some embodiments may utilize vent openings being attachable to tubing that removes the exhaled air away from the work site and possible to a filtration system, the air supply at the work site will thereby be effectively improved in quality. The lower chamber will be basically used for exhalation of carbon dioxide, which can also be aided by connecting the tubing to an evacuation device such as a suction line or fan.

The mask of the present invention provides for a mask that is basically semirigid in both the upper and lower chambers. Primary reason for this design is to incorporate the benefits of the semirigid mask in which the surface of such a mask is kept away from the skin of the wearer, thereby preventing any claustrophobic feeling or difficulty in breathing. The fan type soft mask of the prior art has an inherent flaw in that when air is inhaled, the soft mask material is sucked into the mouth area along with the air. The present invention, by utilizing the semirigid construction in the upper chamber will not experience that problem.

The present invention provides for a redesign of the filtration aspect of the mask. It establishes three areas of filtration. A primary filtration area whereby the most effective filtration must be accomplished. This is primarily in the center area of the mask over the nose, nasal passages and mouth. The second filtration area is located around the primary area, which is in the cheek area of the face. The third filtration area is mostly located in the fringe areas. It is generally acknowledged that the main area of filtration must be in the center of the mask. The present invention will incorporate a rugged, high surface area, created by peaks and valleys in the surface of the mask in this primary area. Larger particles will deposit on the peaks, which may have adhesive characteristics and smaller particles, usually viruses, bacteria and gases, will be picked up in the valley area. The present invention also acknowledges that when these particles impinge upon the mask surface that it would be beneficial that they be retained there rather than reintroduced into the area again. The present invention will incorporate a mantle projection extending outwardly from the surface of the lower chamber to provide a measure of protection to the breathing zone. The mantle having an adhesive band section which, besides trapping and retaining particles, can be manufactured so as to indicate color change. This color change is a visual indicator of when the mask needs changing. It is advisable that the mask be changed frequently, and the changing color will serve as a reminder to do so.

The present invention will improve visibility by eliminating fogging to the wearer's glasses. The mask of the present invention will encourage the wearer to take in air only in the upper chamber and to discharge the warm, moist exhaled breath in the lower chamber. Removing spent air via the lower chamber through venting flaps or tubing will by design prevent fogging of wearer's glasses.

The present invention realizes that some procedures will require an increased level of safety for the health personnel and thereby it is acknowledged that often it is desirable to be able to place additional insertion pads directly into the chambers.

Also an embodiment of the present invention will have means for changing filtration pads without discarding the entire mask. This will involve making the frame of the basic mask reusable. The frame therefore could be manufactured of a cloth-covered sponge material molded about the perimeter. This would make it flexible and adaptable to irregularities of the face and also provide increased comfort and sealing, while also allowing for the discarding of less expensive filtration materials. The frame will utilize periphery clips the entire perimeter, while the reusable filter pads will have cooperating curved recesses for press-fitting onto the frame (in a manner that a lid snaps onto a cup). This can permit use of a higher quality material, one that is more comfortable to the skin and yet still provide a mask with disposable filtration elements.

The present invention will have means for allowing the user to snap protective shields, light deflection shields, and tinted shields. The protective shield is a first line of defense from air borne particles which fly from the work site. The shield is pitched away from the face and mask, to prevent closure, sweating and breathing difficulties. The shields can also provide a measure of protection from ultraviolet rays, especially those rays that are used in curing of composite materials, fiberoptic lights and the bright lights illuminating the field.

The present invention will have vent flaps which open and close on pressure gradients. The vent flaps are located in both chambers. The mask itself extending further to the sides of the face than prior art masks. This enables the mask to be more uniform and easier to adapt a seal therein.

The present invention will have means for attaching tubing which is positioned whereby the spent breath can be evacuated from the lower chamber. A powered device such as a suction line, fan or filtration system can be added to the distal end of the tubes for increased suction or ventilation.

An important object of the present invention is to provide a comfortable mask which will adapt to any size or shape face.

Another object of the present invention is to provide dual chambers, one mainly for inhalation and the other mainly for exhalation.

Another object of the invention is to incorporate the benefits of both semirigid mask materials with a perimeter frame comprising of comfortable, more durable materials.

An important object of the present invention is to utilize an adhesive band section that will not only entrap contaminants but which will retain them, and will indicate by color change when the mask needs to be changed.

An object of the present invention is to utilize a high surface area in the primary filtration area, whereby peaks and valleys in the outer surface will substantially increase the surface filtration area.

Another object of the present invention is to provide vent flaps and vent openings for the evacuation of the spent carbon dioxide. The vents being positioned whereby the venting will be directed posteriorly.

Still another object of present invention is to provide a mask that will have means for adapting facial protective shields, reflective shields and tinted shields.

Another object of the present invention is to provide a frame type gasket comprising of soft cloth, soft paper, or sponge like material for contact with the face, for enhanced conformation with different facial configurations and irregularities.

Another object of the present invention is extending the mask further to the sides of the face for better sealing.

Another object of the present invention is to provide a mask that can be manufactured of inexpensive components thereby providing a mask that will be economical to the user.

These and other objects will become readily apparent upon further review of the following specification and drawings.

DETAILED DESCRIPTION OF THE PREFERRED EMBODIMENT

Figure 1:
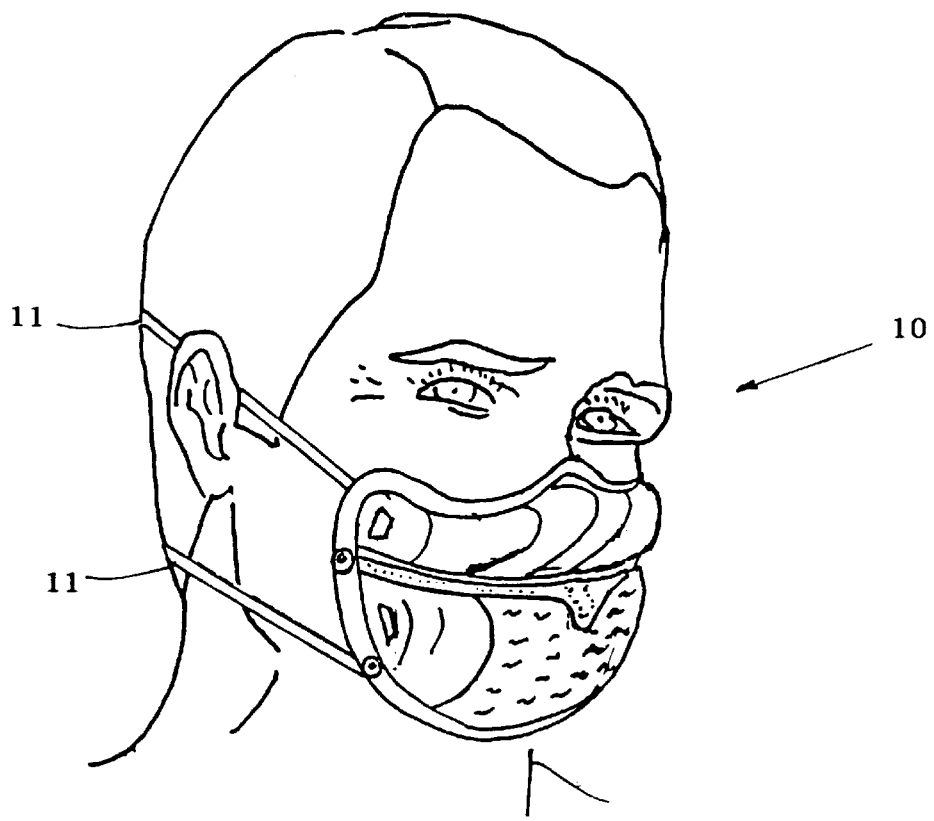
FIG. 1 is a perspective view of the dental mask installed over the face of a wearer.
Figure 2:
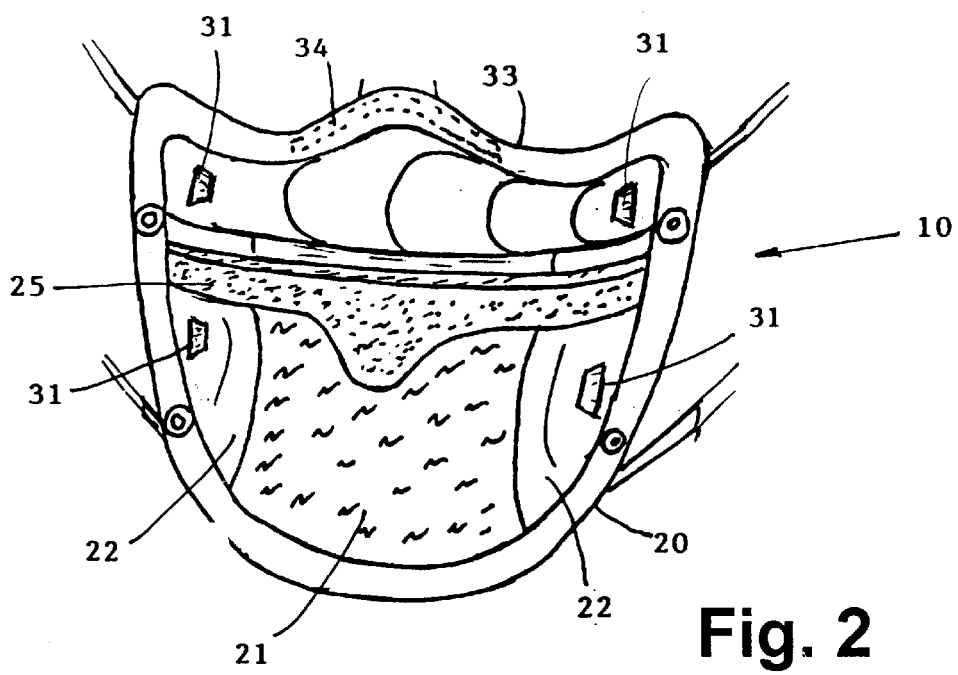
FIG. 2 is a front view of the mask of the present invention showing the mask in position against the face of the wearer.
Figure 3:
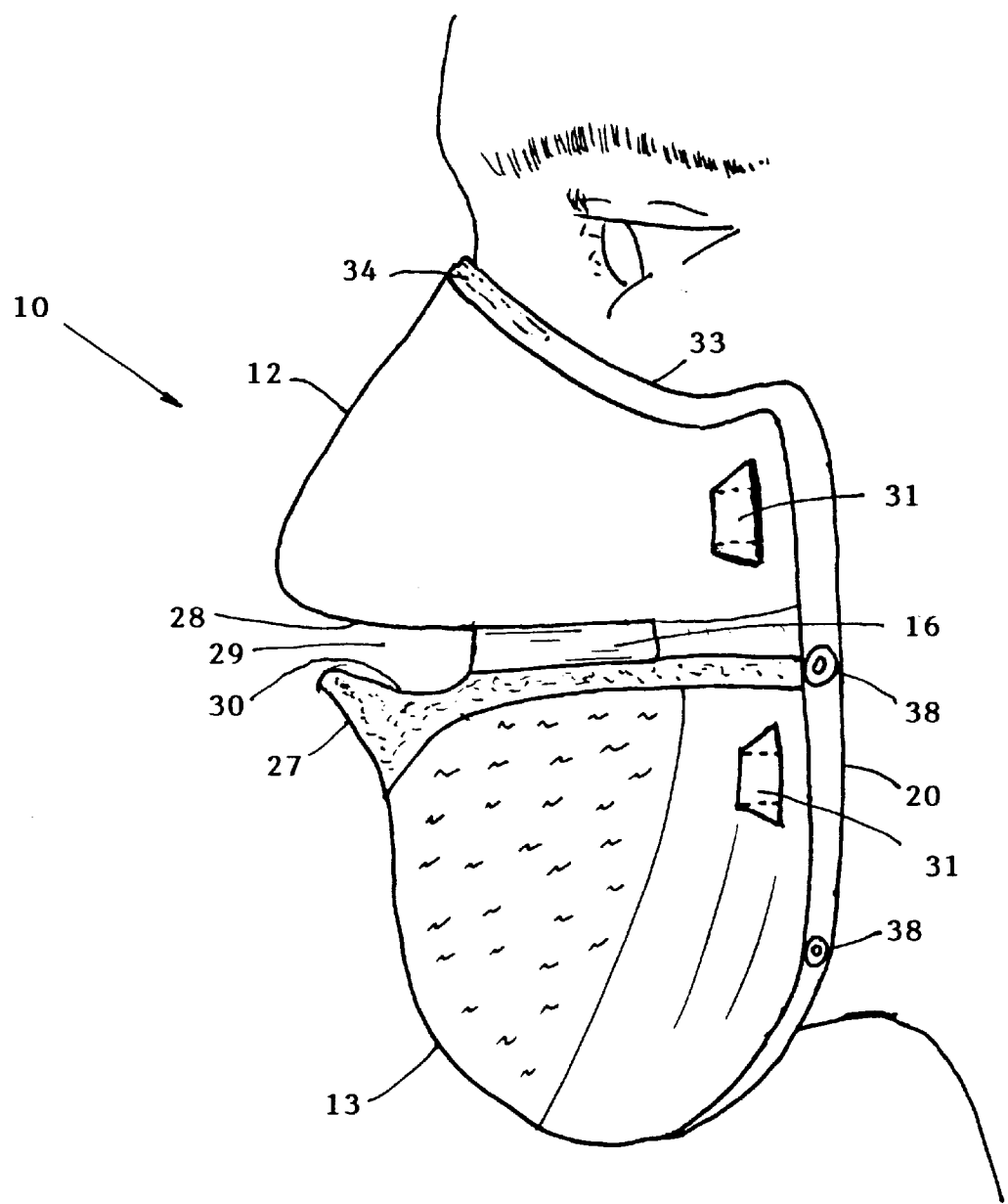
FIG. 3 is a side view of the mask in position against the face of the wearer.

Referring now to the drawings, FIGS. 1–8 illustrate a dental mask of the preferred embodiment. Like structures will be designated with like numerals throughout. FIG. 1 is a perspective view of the dental mask generally designated 10, installed to be worn over the nose and mouth of the wearer. The mask 10 is secured to the wearer by tie strings 11. The mask 10 as shown has tie strings 11 made of elastic material to provide a snug fit and this elasticity provides sufficient flexibility to allow a single size tie to accommodate a range of head sizes. In lieu of the tie strings 11, a single elastic band could be used without deviating from the inventive concept. It is also appreciated that a pair of elastic loops designed to project over the ears of the wearer would also be deemed adequate for the present invention.

Figure 4:
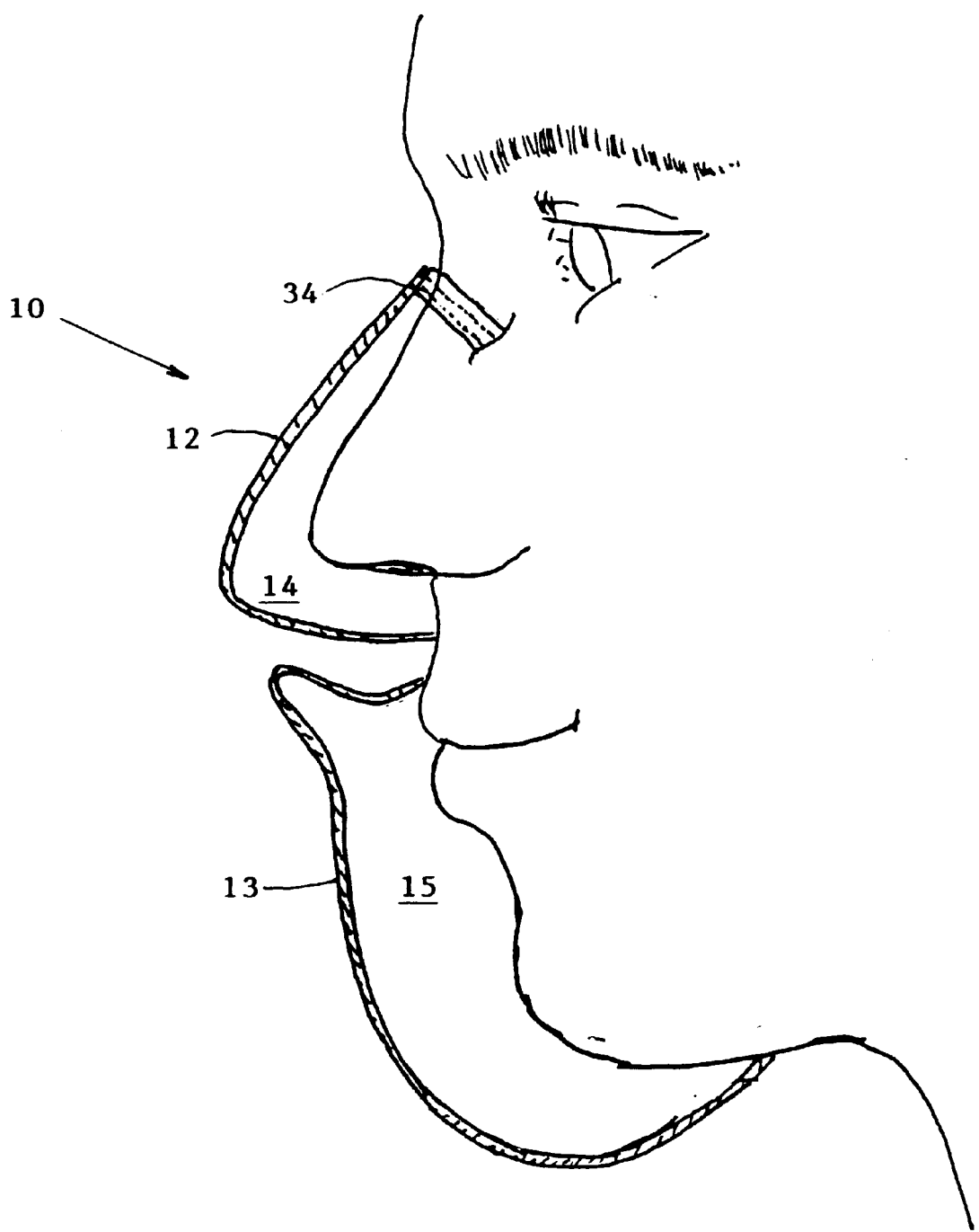
FIG. 4 is a partial cross-sectional view illustrating the dual chambers of the mask.

Mask 10 is designed to protect the wearer from the flow of aerosols, viruses, bacteria, liquids, dusts and other airborne contaminants that are regularly found in dental offices. Aerosols are often by-products of microbial solutions and can be the most hazardous of all contaminants. Mask 10 is constructed so as to include two separate portions, an upper filtration portion 12 and a lower filtration portion 13. Defined within the inner surfaces of the portions 12 and 13 is an upper inhale chamber 14 and a lower exhale chamber 15 repectively. These chambers 14 and 15 are kept isolated from each other by a philtrum band 16. This band 16 has an elasticity that easily conforms to the philtrum area of the face to form a comfortable yet effective seal between the chambers. FIGS. 1–4 depict this seal with FIG. 4 best describing the philtrum band 16 and the two chambers 14 and 15. FIG. 4 illustrates that the philtrum band 16 is comprised of an elasticized soft material that forms the barrier between the upper and lower portions 12 and 13. Mask 10 is made from conventional filtration materials and is designed to offer the advantages of both semirigid and soft masks. Upper portion 12 is basically semirigid while the lower portion 13 is a combination of the semirigid and the softer pleated materials of the fan type masks.

The inventive concept of the dual chambers 14 and 15 is to allow the wearer to breathe fresh air through the nose which is within the confines of upper chamber 14, and to exhale breath containing the high levels of carbon dioxide through the mouth via lower chamber 15. Mask 10 is designed to overcome the problem of single chamber masks wherein the exhaled breath is mingled with the inhaling air. With prior masks the wearer is constantly inhaling his own spent carbon dioxide along with new air. With the body requiring a certain amount of oxygen to survive, this can lead to the wearer requiring more breaths to obtain the needed supply of oxygen. The lack of necessary oxygen can cause hypoxia and the inherent drowsiness, fatigue, apathy, inattentiveness and overall reduced work capacity.

Figure 8:
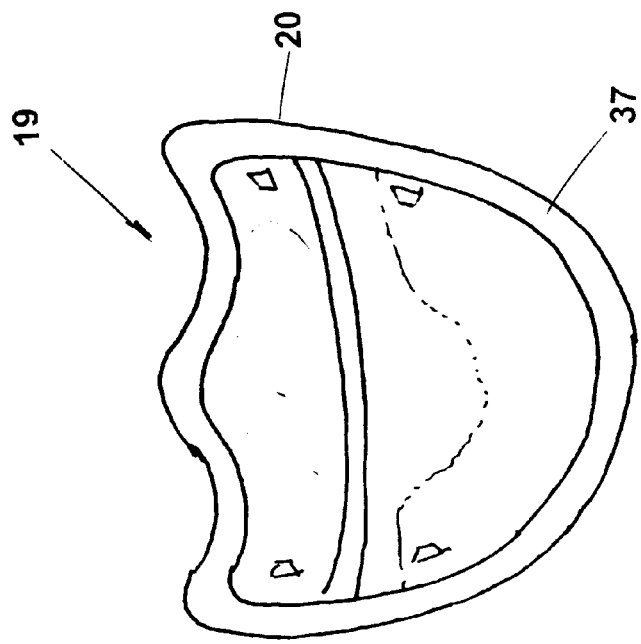
FIG. 8 is a cross sectional view of the periphery clips of the frame and the insertion section of the disposable pad.
Figure 8:
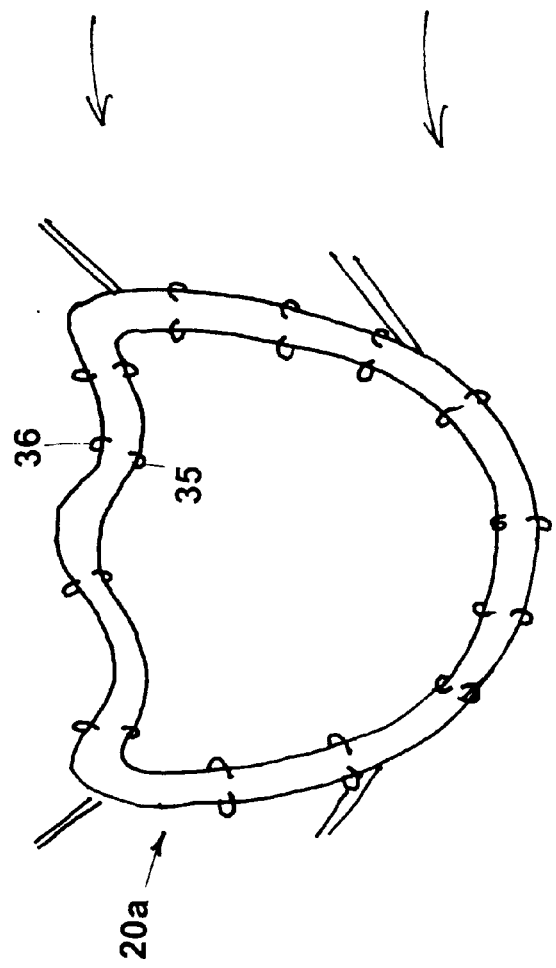

Mask 10 is designed to be used as a disposable item. But, it also has an optional design, whereby a gasket-like frame 20a can be reusable. The frame 20, of the preferred embodiment, has a more substantial consistency than the rest of the mask 10. This can be accomplished by merely increasing the plys of material. In the optional design the upper portion 12, lower portion 13 and philtrum band 16 constitute a replaceable and removable filtration pad 19 which utilizes conventional well-known means for placement to a frame structure 20. Thus the wearer can replace the removable pad 19 when necessary, minimally once for each new patient. The basic frame 20 would be manufactured primarily with comfort as the main goal, as it is the frame 20 that must seal with the face, and thereby be compatible with the skin of the wearer. In the basic unit, the frame 20 would be an integral part with upper and lower portions 12, 13 and philtrom band 16, thereby making the entire mask disposable as a unit. Frame 20a in the optional embodiment would be made from materials selected because of comfort to the wearer, these materials comprising of cloth, sponge, foam or paper. As shown in FIG. 8, frame 20a be reusable and similar to a gasket type structure, accepting disposable pads 19 in the same manner as snapping a lid onto a plastic cup. The frame 20a will include plastic or metal curved clips, inner periphery clips 35 and outer periphery clips 36 which are made by turning up the edges. The replaceable pad 19 would have an insertion edge 37 about the perimeter that press-fits into the clips 35 and 36.

Some procedures require greater filtration protection than do others. It is suggested that replaceable filtration inserts be used which are but sheets of filtration material that the wearer can simply place into the mask in the area of greatest need. This would be in the nasal area and in the mouth section. They would be made of shapes and contours that would readily fit into the inner mask.

The upper filtration portion 12 is comprised of a semirigid molded fibrous porous filtration material. The semirigid material can be selected from a number of conventional fibrous filtration materials. The semirigid construction prevents the material from being sucked against the face of the wearer when he/she draws a breath of fresh air. Philtrum band 16 is integral with the bottom of upper portion 12.

Philtrum band 16 is comprised of a smoother fibrous material having an elastic or moldable material to hold it sealingly against the philtrum area of the wearer to prevent any intermingling between chambers 14 and 15. The primary filtration section 21, which is located at the nose and mouth areas, has the greatest amount of filtering capacity. In upper portion 12 this will significantly aid the wearer in breathing the cleanest air that is available. The introduction of fresh air without the intermingling of exhaled breath enables the wearer to breathe at a rate close to his/her normal breathing rate. Thus the main purpose of the present invention, which is to eliminate the dangers of hypoxia, is thereby averted.

Figure 7:
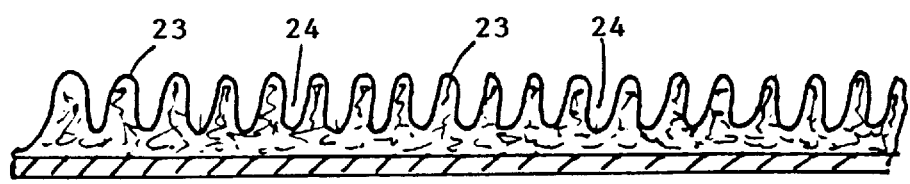
FIG. 7 is a cross-sectional view of the primary filtration material having a peak and valley geometric shape.

Lower filtration portion 13 is made from a combination of semirigid and the softer pleated fibrous filter materials. The primary filtration section 21, which has been designated as requiring the highest level of filtration, is generally semirigid. Whereas the secondary filtration section 22, which is the area about the cheeks and chin, is basically manufactured of the semi-rigid to conventional pleated type materials. Since the major function of lower chamber 15 is to exhale spent breath and because the primary area 21 is semirigid to maintain chamber integrity, the problem of sucking in the mask 10 when drawing a breath is eliminated. In primary filtration section 21, the filtration material has a topography consisting of peaks 23 and valleys 24 as illustrated in FIG. 7. Peaks 23 entrap the largest particles while valleys 24 provide protection against the smaller particles such as those of gases, viruses and bacteria.

In an area just below and integral with the philtrum band 16 is an adhesive band section 25 extending across the front surface 26 of the lower portion 13. The adhesive band section 25 having the ability to not only filter airborne contaminants but to hold them to its surface. Conventional adhesive materials are available in the marketplace that will indicate by color change the extent of saturation in the filtration material. This will let the wearer know when to change the removable filtration pad 19, filtration inserts or entire mask 10.

Extending upwardly and outwardly from the top of the lower portion 13 is a mantle projection 27 which is contoured to protect the nasal breathing section 28. The adhesive band section 25 covers the entire mantle projection 27 which is designed to reduce the amount of contaminants into the nasal breathing canal 29. Recessed into the breathing canal 29 is a reservoir concavity 30 which functions to provide an increased in the volume of air available beneath the nasal passages.

Both the upper and lower portions 12 and 13 have one-way vent flaps 31 disposed on each side of the mask 10 for venting spent breath posteriorly. These vent flaps are but slits cut on three sides to allow the flap 43 to open upon increased internal pressure from exhalation. In addition to the vent flaps 31, optional tubing sections 32 may be connected that will exhaust the spent breath away from the work site. The tubing 32 should be extremely lightweight as it must be supported by the mask 10. It is well known in the art to support such tubing 32 by clipping to the side frames of glasses or safety goggles. It is to be appreciated that tubing 32 could be connected with a power driven means, such as a suction line, fan or filtration system to aid the evacuation of the spent breath.

As previously discussed, frames 20 and 20a can be made from a comfortable yet sturdy material such as a cloth covered sponge, foam or paper. The top section of frames 20, 20a has an elongated nose ridge 33 contoured to conform in a sealing relationship to the shape of the wearer's nose. The nose ridge 33 contains therein an elongated strip of malleable metal 34 or moldable material longitudinally transposed therein for forming a tight seal between mask 10 and the wearer's face. Suitable for use as a malleable metal 34 would be a thin strip of aluminum, thin gauge steel or even plastic overlaid by a cloth material or soft filtration materials as used in the fan type masks. Because of the design of mask 10, wherein it is in the lower chamber 15 that the warm moist breath is removed to reduce fogging of glasses, a tight seal is not as important as it is at the top of the mask 10. However, the malleable strip 34 does not only serve as another measure of protection from fogging but as another measure of support for the mask 10 which primarily depends upon tie strings 11 for support.

Mask 10 will have mushroom shaped buttons 38 integrally mounted about the top surface 39 of frames 20, and 20a. The present invention utilizing four such buttons 38, one button 38 on either side of the philtrum band 16, and one button 38 on either side of lower portion 13. Buttons 38 will mountingly support accessory items which are discussed herewith.

Figure 5:
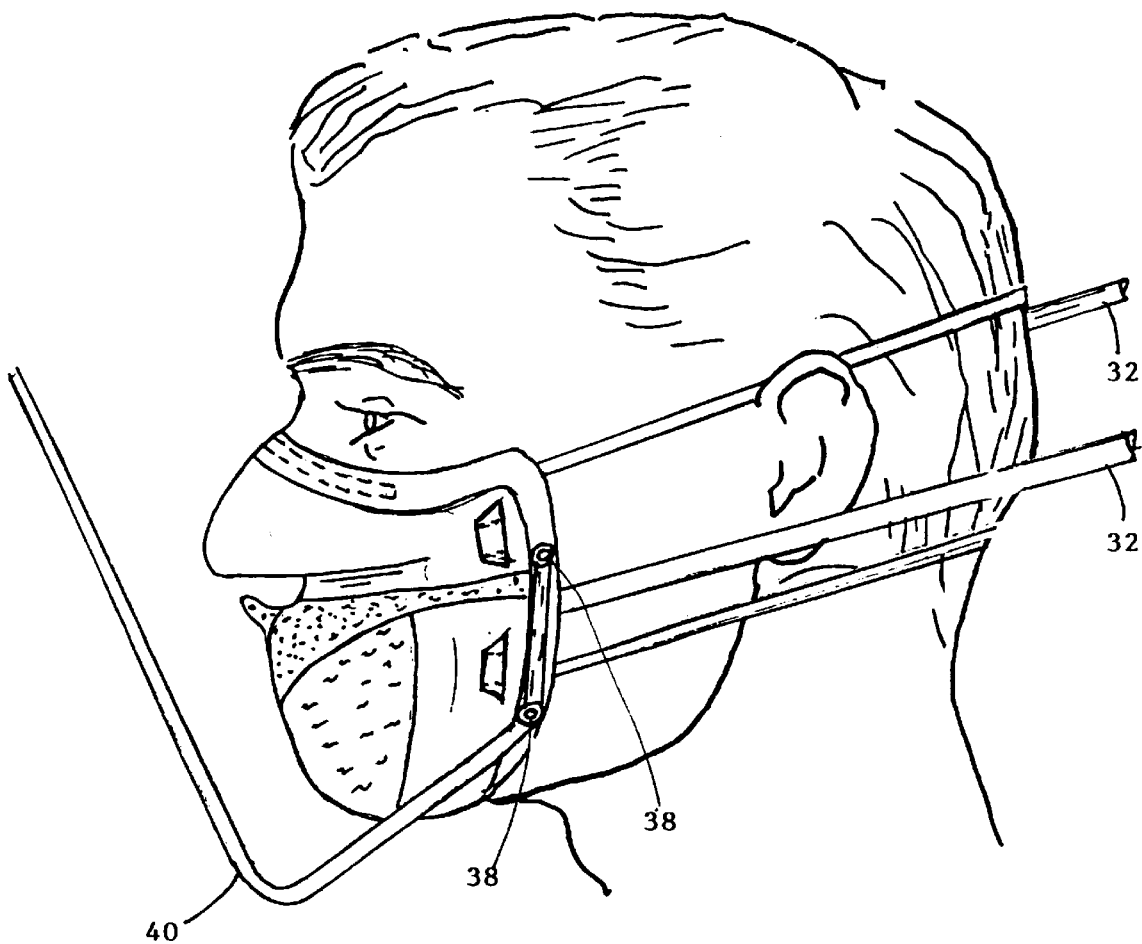
FIG. 5 is a side view of an embodiment of the present invention illustrating a protective shield snap-fitted to the frame of the mask.

FIG. 5 illustrates a side view of a fluid-impervious transparent protective shield 40 attached to corresponding buttons 38 on frames 20 and 20a. The shield 40 will have well known means (not shown) for friction fitting upon the buttons 38 and will comprise a shield 40 that is extended at appoximately 60° to horizontal. This angle will provide protection for the eyes and face from splattering of blood and other contaminated fluids of a seated dental patient. It also will allow more air circulation, less sweating and easier breathing than that available from vertically oriented shields of the prior art. Transparent shield 40 can be an optically clear plastic film, such as polyester or polycarbonate. Preferably shield 40 will be treated with a tinted coloring material to protect the wearer from harmful light rays used in curing procedures. Shield 40 may be coated with an anti-fogging agent to prevent the wearer's breath from fogging up the shield 40 when mask 10 is worn, however with the design mask of the present invention this would be minuscule, since the exhaled breath is expelled away from the work site.

Figure 6:
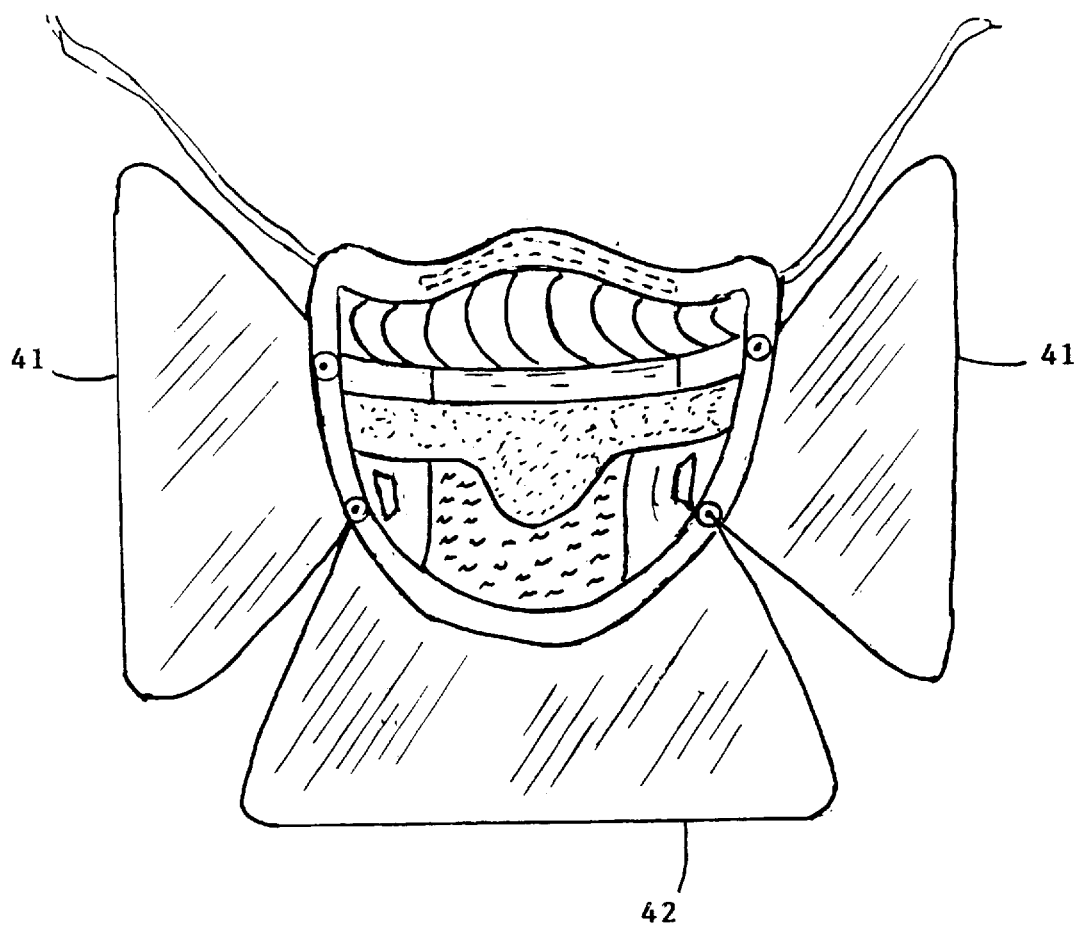
FIG. 6 is a front elevational view of the mask with an embodiment employing protective panels attached therein.

Other accessory items to be utilized by the present invention are illustrated in FIG. 6 which depicts mask 10 having a pair of protective side panels 41 fitted to the buttons 38 and a protective chin panel 42 similarly fitted to the buttons 38. These accessories offer the wearer a wider area of protection than could be obtained with only the mask 10. Modifications to these accessories would be to have the panels made of a reflective material whereby the light from the field would be directed towards the work site, and hook-ups to evacuation and filtration systems.

While there has been and described what are at present considered the preferred embodiments of the invention, it will be apparent to those skilled in the art that modifications and changes can be made therein without departing from the scope of the present invention as defined by the appended claims.

I claim:

1. A dental mask comprising:
   an upper filtration portion having an upper inhalation chamber defined therein for covering a nose area;
   a lower filtration portion having a lower exhalation chamber defined therein for covering a mouth area;
   an elasticized philtrum band extending between and integrally connecting the upper portion to the lower portion, the band adapted to form an impervious gas tight seal between the two chambers;

a frame integrally encasing the upper portion, the lower portion and the philtrum band;

the upper filtration portion of the frame formed of semi-rigid porous fibrous material being spaced away from wearer's face and including an elongated nose ridge contoured to conform to the wearer's nose, an elongated malleable moldable strip longitudinally disposed within the nose ridge for supporting the mask and adapted to create a seal between the mask and the wearer's face; and the lower filtration portion comprising:
 a front surface,
 a semi-rigid primary section having a porous fibrous material disposed approximately in the center of the lower filtration portion,
 a topography of peaks and valleys on the front surface of the primary section to effectively increase the surface area, wherein large fluid particles are filtered in the peak areas and relatively smaller particles such as viruses, bacteria and gases are filtered in the valley areas,
 a mantle projection extending upwardly and outwardly from the upper lower portion, the mantle operative as a protective barrier for breathing area, the mantle cooperating with the nasal breathing area to define a nasal canal, a reservoir concavity formed in the nasal canal section of the mantle for increasing the air supply directly beneath the nasal breathing area, and
 means for retaining particles to the front surface, the retaining means further comprising an adhesive band section covering the mantle projection and extending to the frame;
 means for indicating when material is saturated with contaminated particles, and indicating means further comprising a color changing chemical immersed in the adhesive band section,
wherein the wearer, by breathing through the upper filtration portion and exhaling through the lower filtration portion, will substantially eliminate rebreathing of wearer's own exhaled breath.

2. The mask according to claim 1, wherein the mask comprises a plurality of vent flaps perforating from the sides of the mask, the vent flaps adapted to open in response to the increased pressure of exhausted breath, wherein the breath is discharged posteriorly.

3. The mask according to claim 1, wherein the frame further includes:
 a top surface;
 a plurality of attachment buttons disposed on the top surface;
 a pair of protective side panels, each side panel having friction-fit means for removably snap-fitting the side panels to the corresponding attachment buttons of the frame; and
 a protective chin panel having friction-fit means for removably snap-fitting the chin panel to the corresponding attachment buttons of the frame, whereby the panels will offer increased protection to the wearer beyond the immediate facial area.

4. The mask according to claim 3, wherein the panels are of a refractive material for reflecting light back to the work site.

5. A dental mask comprising:
 an upper filtration portion having an upper inhalation chamber defined therein for covering a nose area;
 a lower filtration portion having a lower exhalation chamber defined therein for covering a mouth area;
 an elasticized philtrum band extending between and integrally connecting the upper portion to the lower portion, the band adapted to form an impervious gas tight seal between the two chambers;
 a frame integrally encasing the upper portion, the lower portion and the philtrum band;
 wherein the frame further includes:
  a top surface;
  a plurality of attachment buttons disposed on the top surface; and
  a fluid impervious transparent shield having friction-fit means for removably snap-fitting the shield to the corresponding attachment buttons of the frame, the shield adapted to be at an angle generally about 60 degrees from a horizontal plane,
 whereby the shield will afford protection for the wearer's entire face against airborne contaminated fluids without being uncomfortably close to the face area.

6. The mask according to claim 5, wherein the protective shield is tinted to protect against harmful rays arising during some curing procedures.

7. A dental mask having a removable filtration pad, the mask comprising:
 (A) a frame encasing the filtration pad, the frame including:
  a top surface,
  an inner periphery clip about the inner perimeter of the frame,
  an outer periphery clip about the outer perimeter of the frame,
  the clips defining an attachment means for the filtration pad;
 (B) the removable filtration pad comprising:
  an upper filtration portion having an upper inhalation chamber defined therein for covering nose area;
  a lower filtration portion having a lower exhalation chamber defined therein for covering mouth area;
  an elasticized philtrum band extending between and integrally connecting the upper portion to the lower portion, the band being adapted to form an impervious gas tight seal between the two chambers, an insertion section about the perimeter comprising a projection for snap-fitting into the clips of the frame,
 whereby the wearer can periodically replace the filtration pad when the need arises and yet still be able to continue to use the original frame, and whereby the wearer, by breathing in air through the upper portion and exhaling through the lower portion, can substantially eliminate rebreathing his/her exhaled breath.

8. The mask according to claim 7, wherein the mask further includes at least one tie string for securing the mask to the wearer's head.

9. The mask according to claim 7, wherein the upper section of the frame includes an elongated nose ridge contoured to conform to the wearer's nose, an elongated malleable moldable strip longitudinally disposed within the nose ridge for supporting the mask and adapted to create a seal between the mask and the wearer's face.

10. The mask according to claim 7, wherein the upper portion of the pad is formed of semi-rigid porous fibrous material being spaced away from the wearer's face.

11. The mask according to claim 10, wherein the lower portion of the pad comprises:
 a front surface;
 a semi-rigid primary section having a porous fibrous material disposed approximately in the center of the lower portion;

the front surface of the primary section having a topography in the shape of peaks and valleys wherein large fluid particles are filtered in the peak areas and relatively smaller particles such as viruses, bacteria and gases are filtered in the valley areas;

a mantle projection extending upwardly and outwardly from the top of the lower portion, the mantle operative as a protective barrier for a nasal breathing area, the mantle cooperating with the nasal breathing area to define a nasal canal, a reservoir concavity formed in the nasal canal section of the mantle for increasing the availability of air directly beneath the nasal breathing area;

a strip of adhesive tape disposed upon the front surface for retaining particles to the surface of the tape; and a color changing chemical immersed in the tape to indicate a level of saturation of the mask.

12. The mask according to claim 11, wherein the mask comprises a plurality of vent flaps adapted to open in response to the increased pressure of exhausted breath, whereby the exhausted breath is discharged posteriorly.

13. The mask according to claim 7, wherein the frame includes:

a plurality of attachment buttons disposed on the top surface; and a fluid impervious transparent shield having friction-fit means for removably snap-fitting the shield to the corresponding attachment buttons of the frame, the shield adapted to be at an angle generally about 60 degrees from a horizontal plane, whereby the shield will offer protection for the wearer's entire face against airborne contaminated fluids.

14. The mask according to claim 13, wherein the protective shield is made from tinted materials to protect the wearer from harmful rays such as those used in curing procedures.

15. The mask according to claim 7, wherein the frame includes:

a plurality of attachment buttons disposed on the top surface of the frame;

a pair of protective side panels, each side panel having friction-fit means for affixing the panels to the corresponding attachment buttons of the frame; and a protective chin panel having friction-fit means for affixing the chin panel to the corresponding attachment buttons of the frame, whereby the panels will offer increased protection to the wearer beyond the immediate facial area.

16. The mask according to claim 15, wherein the panels are of a refractive material for reflecting light back to the work site.

* * * * *